United States Patent
Wamsiedler et al.

[11] Patent Number: 5,614,677
[45] Date of Patent: Mar. 25, 1997

[54] DIAPHRAGM GAGE FOR MEASURING THE PRESSURE OF A FLUID

[75] Inventors: Ralf Wamsiedler, Oberursel; Ralf Wojke, Frankfurt; Walter Pieper, Florstadt; Horst Christmann-Braun, Kelkheim, all of Germany

[73] Assignee: Fresenius AG, Bad Homburg, Germany

[21] Appl. No.: 448,831

[22] Filed: May 24, 1995

[30] Foreign Application Priority Data

Jun. 3, 1994 [DE] Germany .................. 44 19 593.1

[51] Int. Cl.⁶ .................. G01L 7/08; G01L 9/00
[52] U.S. Cl. .................. 73/715; 73/723
[58] Field of Search .................. 73/715, 716, 723; 128/675, 748; 92/96, 98 R

[56] References Cited

U.S. PATENT DOCUMENTS

| | | |
|---|---|---|
| 4,185,641 | 1/1980 | Minior et al. ................ 73/723 |
| 4,541,282 | 9/1985 | Auerweck et al. ............ 73/715 |
| 4,856,340 | 8/1989 | Garrison ........................ 73/715 |
| 4,885,983 | 12/1989 | Zavoda ........................... 73/715 |

FOREIGN PATENT DOCUMENTS

| | | |
|---|---|---|
| 0130441 | 1/1985 | European Pat. Off. |
| 0303979 | 2/1989 | European Pat. Off. |
| 2930869 | 3/1980 | Germany . |
| WO93/24817 | 12/1993 | WIPO . |

Primary Examiner—Richard Chilcot
Assistant Examiner—William L. Oen
Attorney, Agent, or Firm—Henry M. Feiereisen

[57] ABSTRACT

Apparatus for measuring the pressure of a fluid includes a first pressure transmission element in form of a membrane in contact with a pressure sensor, and a second pressure transmission element in form of a membrane which is acted upon by a fluid whose pressure is to be determined. The first membrane has a peripheral area which is pressed against the second membrane in such a manner that the space between the first and second membranes is sealed off from outside and is of a size as small as possible. Both membranes thus move in synchronism in dependence of the fluid pressure so that positive as well as negative pressures can be measured.

19 Claims, 4 Drawing Sheets

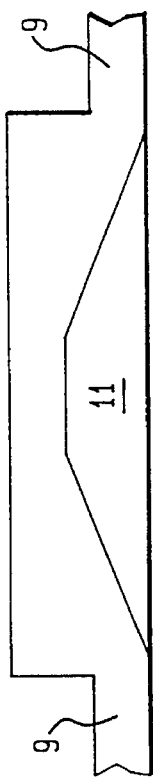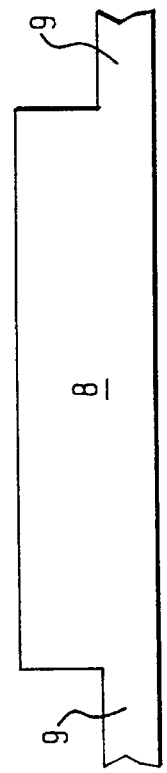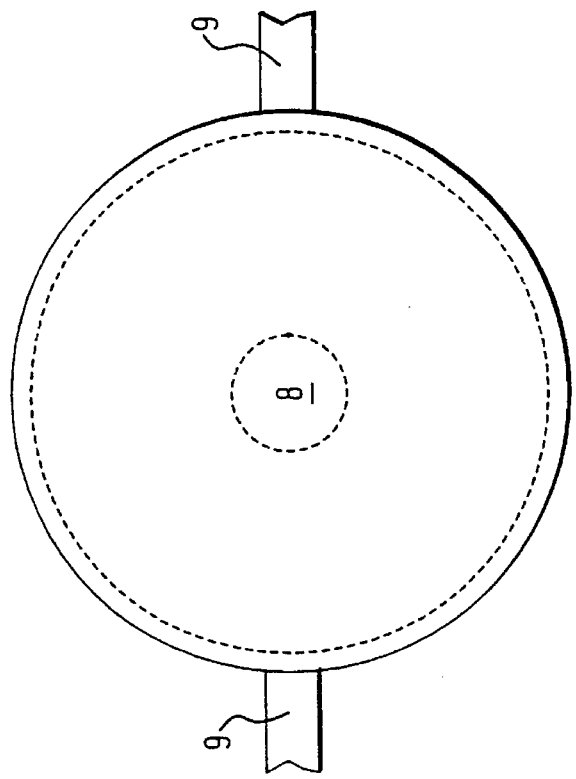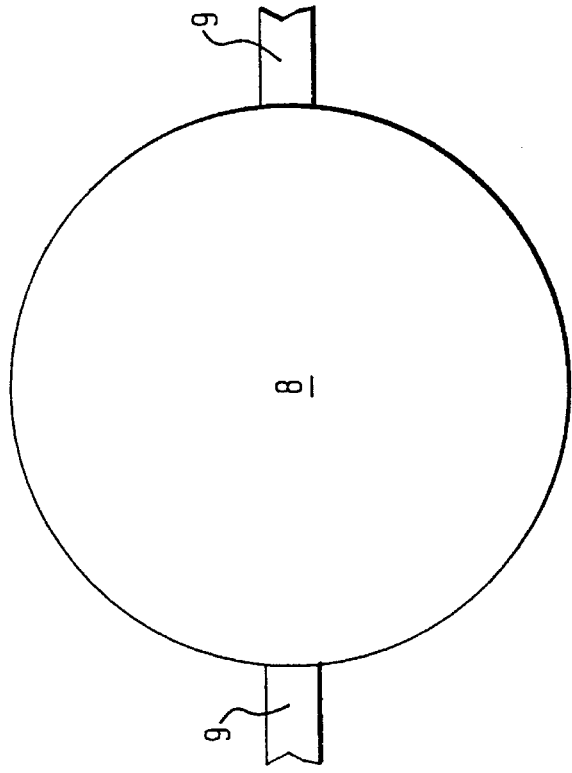

DIAPHRAGM GAGE FOR MEASURING THE PRESSURE OF A FLUID

BACKGROUND OF THE INVENTION

The present invention refers to an apparatus for measuring the pressure of a fluid, and in particular to a pressure measuring apparatus of a type having a pressure sensor which contacts a first pressure transmission element, and a second pressure transmission element which is in communication with the fluid of which the pressure is to be measured.

Such a pressure measuring apparatus is utilized for all kinds of fluids, e.g. in the medical field for pressure determination in extracorporeal blood circulations as encountered during dialysis.

In an apparatus for measuring the pressure of a fluid in a circulation, e.g. of blood in extracorporeal blood circulations, the provision of a branch from the actual circulation of the fluid for measurement is disadvantageous because the simple and clear line configuration of the circulation is lost and the complexity increases the chances of error and the assembly time of the system. Moreover, the arrangement of a branch requires a greater filling volume of the system. Safety concerns necessitate however to reduce the quantity of extracorporeal blood volume to a minimum. Also, a pressure measuring process which operates in a branch of the blood circulation draws a certain blood volume which is retained in a dead space for a relative long period. This extended retention time increases the tendency of blood coagulation and an increased administration of systemic coagulation inhibitors, such as heparin, becomes necessary.

Non-invasive systems do not experience these drawbacks. By measuring the pressure not in a branch but directly upon the tube, the line configuration of the tube system remains clear, the filling volume is only insignificantly increased and the dead space of the branch is omitted.

Tubes, such as blood tubings, have elastic as well as viscous or elasticoviscous properties. While the initial state is recovered after an elastic stress, this is not the case during a viscous modification. An absolute pressure measurement upon the tube is complicated in particular through these viscous properties of the tube material. In order to minimize the impact of the viscosity of the material, the use of a thin membrane is proposed instead of a thick tubing in the area of the pressure measurement. However, problems were experienced in connection with the transmission of the membrane movement upon the pressure sensor. Moreover, a further problem arose also because generally, also very high negative pressures should be detected.

European Pat. No. EP 0 355 373 B1 discloses a fluid-pressure detector, in which a measuring unit detects the expansion or shrinkage of a pillow-like body capable of expanding and shrinking depending on the pressure of the fluid flowing in the pillow-like body. The measurement on the arched surface of the pillow-like body is effected by means of an iron plate, which is attached to the pillow-like body, via a magnet which is detachably secured to the tip of the measuring unit. This detector is complicated because the iron plate is connected with the part conducting the fluid and thus becomes too cost-intensive in one-way systems, such as extracorporeal blood circulations, after a one-time use. Moreover, the inherent inertia of such a system results in a relatively poor sensitiveness of the system.

European Pat. No. 0 330 891 B1 discloses an arrangement for pressure transmission in which an outer casing is divided by a membrane into two separate spaces, with the fluid whose pressure is to be determined flowing through one space, and with a second, auxiliary fluid flowing through the other space. Pressure fluctuations of the fluid are transmitted by the membrane to the second fluid for effecting the actual pressure measurement in known invasive manner. Because of the indirect pressure measurement and because of the inherent inertia, also this system is not very sensitive and reacts in a relatively slow manner.

International patent application WO 93/22641 A1 describes a pressure measuring system in which pressure changes are transmitted from a membrane onto a pressure sensor by a fluid. This system has the same drawbacks as described above, and moreover is relatively complicated and cumbersome to manufacture so that its use is impractical for one-way systems.

European Pat. No. EP 0 200 709 B1 describes a pressure transducer provided with a plate membrane which is permanently attached to a housing and seals the latter against the fluid being measured. The membrane is connected to a measuring element situated in the housing for transmitting the pressure to be determined. An annular area of the membrane is of arched or conical shape in its original state and extends into the interior of the housing, when it is not subject to the pressure being measured. The configuration of the membrane complicates the manufacture and deteriorates the contact between the sensor membrane and the tube membrane.

European Pat. No. 0 130 441 B1 discloses a pressure measuring system which operates without any transfer fluid. The cavity between both pressure transmission elements is emptied or evacuated by a vacuum pump in order to effect a contact of the pressure transmission elements. This system is highly susceptible to failure, very complicated and thus expensive. Moreover, the system is coupled via a tube so that the fluid is conducted through the measuring unit and thus has all those drawbacks of an invasive system as previously described.

German Pat. No. DE-C-29 30 869 discloses a pressure measuring cell by which two membranes are contacted through twisting of the housing parts. Since the pressure measuring cell and the pressure transducer are manually bolted together, the attainable pressure forces between both membranes are relatively low. Moreover, the twisting motion for attachment of both membranes results in a membrane torsion which adversely affects the desired tightness and may even lead to a destruction of the membrane. This however must be prevented under any circumstances when used in the medical field.

SUMMARY OF THE INVENTION

It is an object of the present invention to provide an improved apparatus for measuring the pressure of a fluid, obviating the aforestated drawbacks.

In particular, it is an object of the present invention to provide an improved apparatus for measuring the pressure of a fluid, by which positive pressures as well as negative pressures can be precisely and rapidly detected in a simple manner during a non-invasive measurement.

It is yet another object of the present invention to provide an improved apparatus for measuring the pressure of a fluid, which is easy to produce and to handle and suitable for one-way systems.

These objects, and others which will become apparent hereinafter are attained in accordance with the present invention by pressing the first pressure transmission element in its border area against the second pressure transmission element in such a manner that the space between the first and second pressure transmission elements is sealed against the outside and is as small as possible.

The provision of such a pressure measuring apparatus results in an intimate contact between both pressure transmission elements in a simple manner, thereby enabling a non-invasive measurement of positive and negative pressures at low inertia. The translational force impact in axial direction results in high pressure forces and thus in a superior tightness about the border area as required for underpressure measurement. Moreover, since the pressure forces are introduced in axial direction, the membrane is not subject to torsion which would otherwise adversely effect the tightness of the space between the membranes in the underpressure area and result in a destruction of the membranes.

Preferably, the first pressure transmission element is pressed about its border area against the second transmission element in such a manner that the space between both pressure transmission elements is sealed towards the outside and both pressure transmission elements are arranged directly above each other without inclusion of air or liquid. Suitably, a vacuum exists between the pressure transmission elements to effect a practically inertia-free pressure transmission.

According to another feature of the present invention, the second pressure transmission element is secured in a clamping fixture which has an opening bridged by the second transmission element to enable a communication thereof with the fluid. Thus, a one-way system requires only replacement of the second pressure transmission element, i.e. a membrane, and of the clamping fixture as disposable components of the system. These disposable parts can be manufactured in a cost-efficient manner and recycled.

Suitably, a guide element is provided in opposition to the clamping fixture to position and press the first pressure transmission element against the second pressure transmission element. The first pressure transmission element is in communication with a pressure sensor which, preferably, is urged by a spring element against the first pressure transmission element. Alternatively, the first pressure transmission element may constitute the lower area of the pressure sensor itself. By inserting the first pressure transmission element, which is connected to the pressure sensor, the system is ready for operation.

According to another embodiment of the present invention, the second pressure transmission element is held in the clamping fixture above the opening thereof, e.g. by a tension ring. The clamping fixture may also be provided with an elevation, e.g. an O-ring, so as to guide the second pressure transmission element at a distance above the opening.

Preferably, the second pressure transmission element, the clamping fixture and optionally the elevation are arranged at a pressure measuring chamber which includes two connectors for attachment of a tube and is suitably of cylindrical configuration. The area of the pressure measuring chamber in opposition to the second pressure transmission element may be formed with a volume-reducing elevation, preferably of truncated cone shape, to eliminate dead spaces and to generate a throttle effect.

The apparatus according to the present invention for measuring the pressure of a fluid is generally usable for non-invasive pressure measurement, e.g. in a blood tube system, in particular the blood tube system of a dialyzer.

BRIEF DESCRIPTION OF THE DRAWING

The above and other objects, features and advantages of the present invention will now be described in more detail with reference to the accompanying drawing in which:

FIG. 2 is a side view of a pressure measuring chamber of the apparatus of FIG. 1;

FIG. 2a is a plan view upon the pressure measuring chamber of FIG. 2;

FIG. 3 is a side view of a modified pressure measuring chamber of the apparatus of FIG. 1;

FIG. 3a is a plan view upon the pressure measuring chamber of FIG. 3;

DETAILED DESCRIPTION OF PREFERRED EMBODIMENTS

Figure 1:
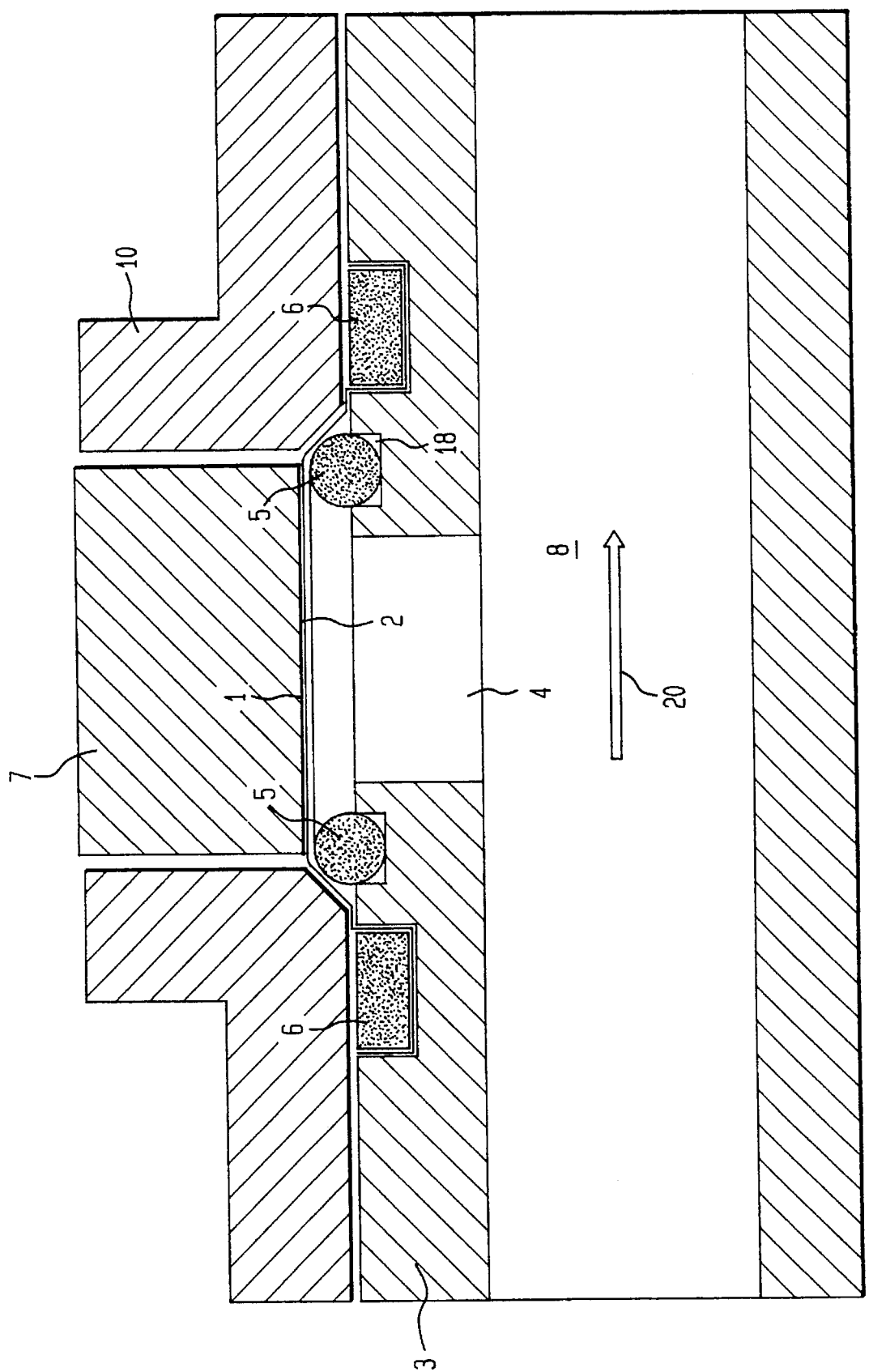
FIG. 1 is a sectional, schematic principal illustration of an apparatus for measuring the pressure of a fluid, in accordance with the present invention.

Throughout all the Figures, the same or corresponding elements are generally indicated by the same reference numerals.

Turning now to the drawing, and in particular to FIG. 1, there is shown a schematic, sectional view of an apparatus for measuring the pressure of a fluid arranged adjacent a pressure measuring chamber 8 which includes two connections 9 (FIGS. 2, 3) for attachment of a tube for circulation of fluid in direction of arrow 20. The pressure measuring apparatus includes a clamping fixture 3 which is provided with a central opening 4 in communication with the pressure measuring chamber 8. Arranged in opposition to the clamping fixture 3 is a guide 10 for receiving a pressure sensor 7 which is located above the opening 4 and registers fluctuations of the fluid conducted in the chamber 8. At its end facing the opening 4, the pressure sensor 7 supports directly or indirectly a first pressure transmission element 1 of suitable material. The pressure transmission element 1 may be a membrane of stainless steel or an element of ceramics, and is called "sensor membrane".

Extending coextensively to the sensor membrane 1 is a second pressure transmission element 2 which is in general a membrane and frequently called "tube membrane". The second pressure transmission element 2 is made of a material which is compatible with the conducted fluid, i.e. in the present example compatible to blood, and which has a sufficient elasticity and pressure resistance in the pressure range at hand. Moreover, the selected material should be able to reverse any deformation and accomplish the required tightness. Examples for the material of the membrane include latex coated with polyurethane, SI, PU, polyolefines, PETB and PVC. In general, the second pressure transmission element 2 is of round configuration, however, other configurations are certainly also conceivable.

The second pressure transmission element 2 is mounted in the clamping fixture 3, e.g. by means of a tension ring 6, in such a manner that the opening 4 is smoothly bridged by the element 2, with the second transmission element 2 and the tension ring 6 effectively forming a seal between the fluid and the upper surface of the clamping fixture 3. Alternatively, the second pressure transmission element 2 can also be cemented onto the clamping fixture 3 if the used materials permit such a connection.

The second pressure transmission element 2 may run smoothly upon the upper edge of the clamping fixture 3 over the opening 4, or, as shown in FIG. 1, may run over an elevation 5 which extends around the opening 4. In a simple embodiment, the elevation is formed by a O-ring placed in a suitable annular groove 18. The elasticity of the elevation 5 and the thin tube membrane 2 creates a plain surface in the raised section of the second pressure transmission element 2, i.e. the area bridging the opening 4 at a distance thereto. In the event, the arrangement of an elevation is omitted, it may be suitable to bevel the upper edge of the opening 4 in the clamping fixture 3 to avoid injury of the second pressure transmission element 2 during movement.

The first pressure transmission element 1, which generally is also provided in form of a membrane, extends above the opening 4 in the area of the tube membrane 2 which is influenced by the pressure fluctuations of the fluid and possibly is extended beyond this area to bear upon the clamping fixture 3, and is forced onto at least the border area of the second pressure transmission element 2 in such a manner that both pressure transmission elements 1, 2 tightly fit upon each other to minimize the space therebetween and to reduce it toward zero. In the ideal case, the spacing between both pressure transmission elements 1, 2 equals zero. Since the area between both pressure transmission elements 1, 2 is not connected to the atmosphere and possibly is evacuated, both pressure transmission elements 1,2 adhere to each other so that the flexible center thereof is sealed off and both pressure transmission elements 1, 2 move in synchronism in dependence of the fluid pressure. Thus, positive as well as negative pressures can be transmitted from the second pressure transmission element 2 to the first pressure transmission element 1, with the transmission of pressure fluctuations between both pressure transmission elements 1, 2 being produced directly without interposed fluid, so that the inertia of the overall system is low and the sensitiveness and accuracy of the measurement is increased.

This requires that the geometry of both pressure transmission elements 1, 2 is suited to each other. As stated above, the first pressure transmission element 1 can be made of various materials and is directly or indirectly attached to the pressure sensor 7 which processes the pressure fluctuations of the fluid as registered by the pressure transmission element 1. As shown in FIG. 1, the pressure sensor 7 is received in the guide 10 and is pressed with its first pressure transmission element 1 either in the area of the elevation 5 or the plain border area around the opening 4 of the clamping fixture 3 against the second pressure transmission element 2, with the elevation 5 or the border area around the opening 4 forming a counterbearing. In particular in the area of the counterbearing, the press force must be sufficiently great to ensure a direct and intimate contact of the pressure transmission elements 1, 2. Advantageously, as shown in FIG. 1, the guide 10 of the pressure sensor 7 serves simultaneously to clamp the tension ring 6.

The second pressure transmission element 2 should be arranged as flat as possible. When attaching a plain (circular) area laterally to a cylindrical tube (the tube with the fluid to be measured), transitions or dead spaces are created which can however be kept to a minimum when dimensioning the second pressure transmission element 2 to not essentially exceed the tube diameter.

Turning now to FIGS. 2 and 2a, there is shown a simple configuration of a pressure measuring chamber 8 of cylindrical configuration, with two tube connections 9 for attachment of a tube. The tube membrane 2 and the sensor membrane 1 are preferably pressed upon each other in the upper area of the pressure measuring chamber 8 which has a relatively large volume and a significantly greater cross section than the tube so that the flow rate will be relatively small. In connection with fluids, such as blood, an increased flow time may lead to changes in the composition, e.g. coagulation, so that the creation of dead spaces is undesired.

FIGS. 3 and 3a show a possibility to increase the flow rate by reducing the volume of the pressure measuring chamber 8 through incorporation of a elevation 11 formed suitably on the side of the pressure measuring chamber 8 opposing the tube membrane 2. The volume-reducing elevation 11 may be of any suitable configuration depending on the form of the pressure measuring chamber 8, e.g. of conical shape or semispherical shape or, as shown in FIG. 3, of truncated cone shape.

Figure 4:
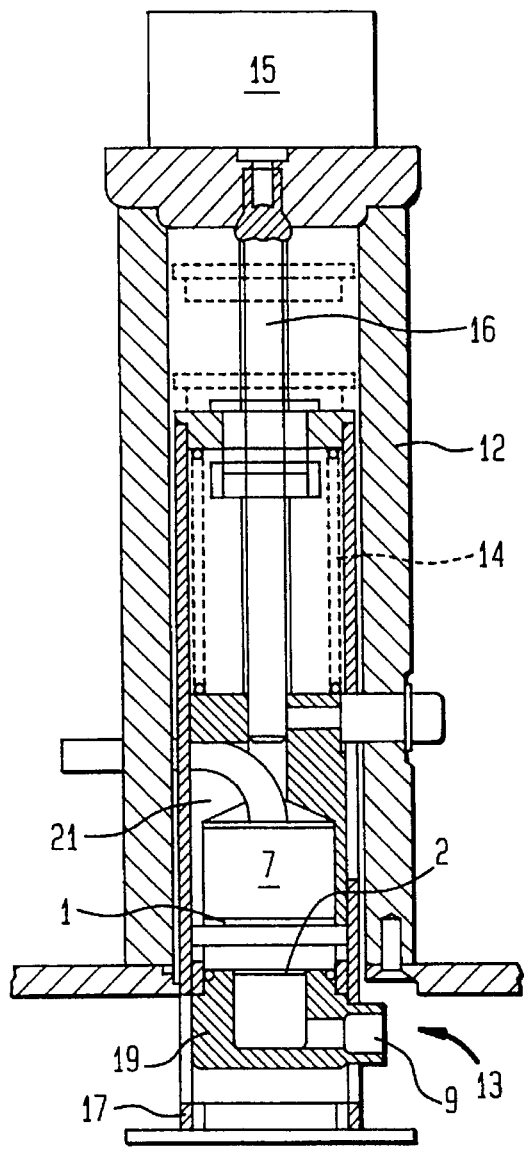
FIG. 4 is a sectional illustration of an exemplified apparatus for measuring the pressure of a fluid, in accordance with the present invention.
Figure 4B:
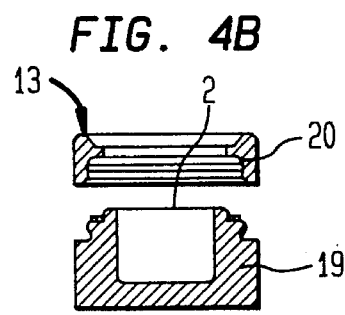
FIG. 4b is an exploded side view of the disposable unit.
Figure 4A:
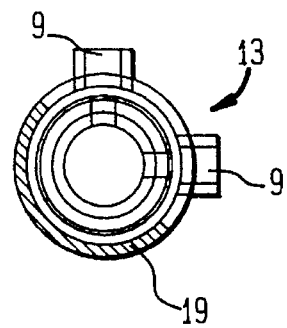
FIG. 4a is a plan view of a disposable unit, constituting one part of the apparatus according to the invention.

Referring now to FIG. 4, there is shown an exemplified embodiment of a pressure measuring apparatus according to the present invention for use in extracorporeal circulations. The pressure measuring apparatus can be divided into two parts, with the first part constituting a disposable unit, generally designated by reference numeral 13 and located in the extracorporeal circulation, and with the second part being located on the side of the apparatus. The disposable unit 13 includes a housing 19 which is closed by a lid 20. The housing 19 is provided with two connectors 9 for attachment of a tube which are angularly spaced by 90°, as shown in FIG. 4a. At its upper end face, the housing 19 carries the slightly prestressed tube membrane 2, e.g. a silicone membrane, as shown in FIG. 4b.

The second part at the side of the apparatus includes a housing 12 which is provided with a central bore 21. Received in the bore 21 is the pressure sensor 7 which is secured in a mounting and biased by a spring element 14, e.g. a helical spring, in direction of the disposable unit 13 for joining the sensor membrane 1 with the tube membrane 2 of the disposable unit 13. A drive 15, e.g. an electric or pneumatic drive, is operatively connected to a spindle 16 which extends axially within the bore 21 and is suitably connected to the mounting for the pressure sensor 7 to disengage the sensor membrane 1 from the tube membrane 2. During coupling operation, the end face of the pressure sensor 7 is pressed with its sensor membrane 1 about its perimeter onto the edge of the tube membrane 2 against a subjacent abutment. The disposable unit 13 is dimensioned in such a manner that the space between the membranes 1, 2 are sealed off against the surrounding and kept as small as possible, ideally zero. This measure ensures that even at high underpressures, a complete tightness and thus a high measuring accuracy is attained.

As further shown in FIG. 4, the disposable unit 13 is received in a drawer-type receptacle 17 which is movable within the bore 21 between three positions, as partly indicated by dash-dot lines. In order to allow placement of the replaceable disposable unit 13, the drawer-like receptacle 17 is fully retracted in direction away from the pressure sensor 7, as shown in FIG. 4 in continuous line. For operation, the drawer-like receptacle 17 together with the disposable unit 13 is then pushed into the bore 21 of the housing 12 towards the pressure sensor 7 until the membranes 1, 2 are coupled or joined. This position is indicated by the lower dash-dot line. In case the pressure measuring unit is idle, the drawer-like receptacle 17 is fully inserted, as indicated by the upper dash-dot line. In this position, the rear end of the drawer-like receptacle 17 extends flush with the front plate of the housing 12, to facilitate a cleaning of the apparatus.

Figure 5:
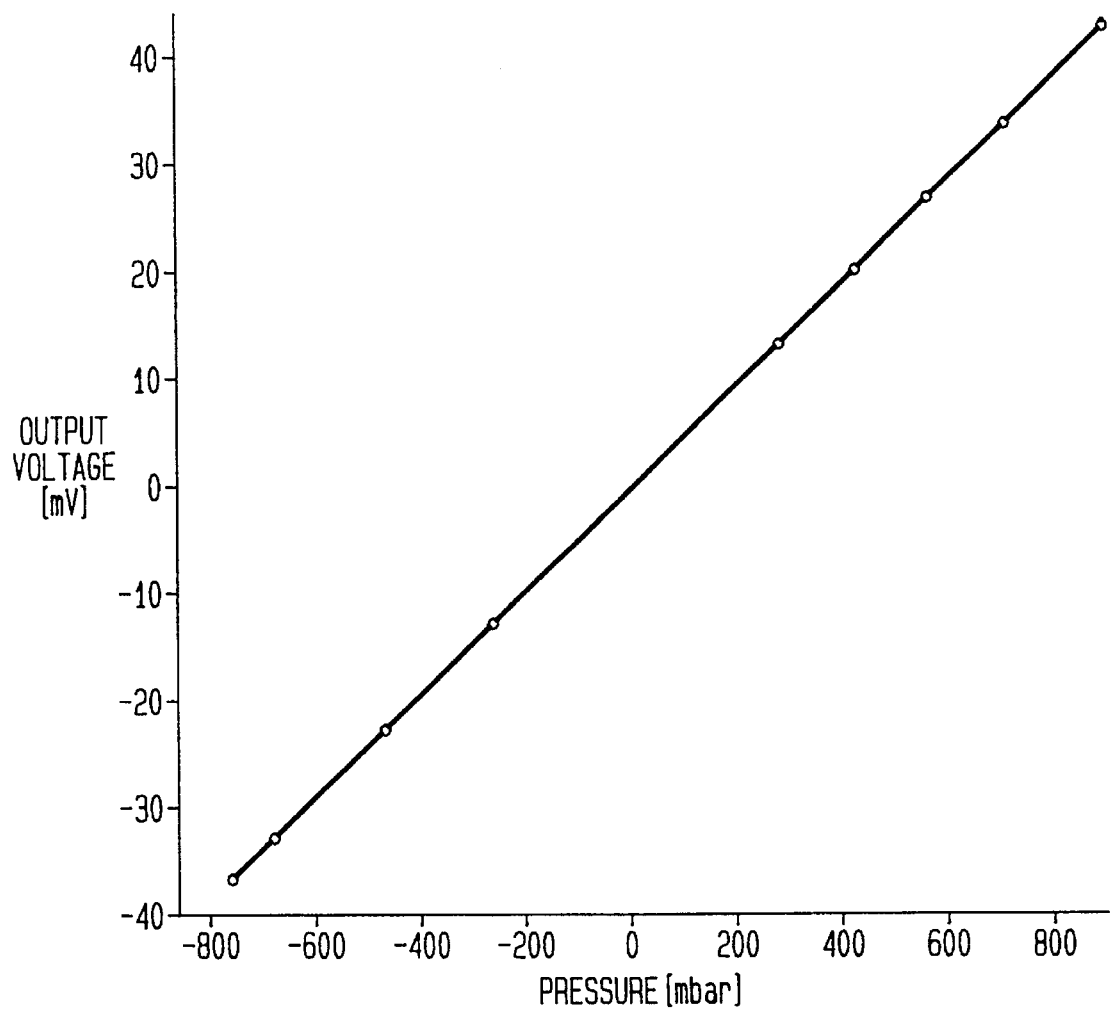
FIG. 5 is a graphical illustration of the output voltage of the pressure sensor as a function of the pressure in the fluid, as determined by the apparatus according to the present invention.

Turning now to FIG. 5, there is shown a graphical illustration of the output voltage of the pressure sensor 7 as a function of the pressure in the fluid, and it can be seen that over a wide range of the fluid pressure, the output voltage extends linear despite the interposed tube membrane 2. The very precise measuring results, also in the negative pressure range, can be attributed to the superior adhesion of both adjoining membranes 1, 2.

While the invention has been illustrated and described as embodied in an apparatus for measuring the pressure of a fluid, it is not intended to be limited to the details shown since various modifications and structural changes may be made without departing in any way from the spirit of the present invention.

What is claimed as new and desired to be protected by Letters Patent is set forth in the appended claims:

We claim:

1. Apparatus for measuring the pressure of a fluid, comprising:
   a first pressure transmission element;
   a pressure sensor operatively connected with said first pressure transmission element; and
   a second pressure transmission element acted on by a fluid, said first pressure transmission element having a border area which is pressed through a translational force in an axial direction against said second transmission element in such a manner that a space between said first and second pressure transmission elements is sealed off from outside and is of a size as small as possible so as to effect a substantially synchronous movement of the first and second pressure transmission elements in dependence of the pressure of the fluid acting on the second pressure transmission element and thereby to allow a direct measurement of the fluid pressure by the pressure sensor.

2. Apparatus as defined in claim 1 wherein said first pressure transmission element is pressed with its border area against said second pressure transmission element in such a manner that the space between the first and second transmission elements is sealed off from outside and both pressure transmission elements are arranged directly above each other without inclusion of air or liquid.

3. Apparatus as defined in claim 1, further comprising a clamping fixture for securing said second pressure transmission element, said clamping fixture having an opening for allowing a communication of said second pressure transmission element with the fluid.

4. Apparatus as defined in claim 1, further comprising a guide mechanism in opposition to said clamping fixture for receiving and pressing said first pressure transmission element against said second pressure transmission element.

5. Apparatus as defined in claim 4, further comprising a spring element for loading said pressure sensor in direction of said first pressure transmission element.

6. Apparatus as defined in claim 3 wherein said second pressure transmission element is secured in said clamping fixture across said opening of said clamping fixture.

7. Apparatus as defined in claim 6, further comprising a tension ring for retaining said second pressure transmission element across said opening of said clamping fixture.

8. Apparatus as defined in claim 6, further comprising an elevation received in said clamping fixture, said elevation projecting beyond and extending around said opening, with said second pressure transmission element being stretched across said opening of said clamping fixture via said elevation.

9. Apparatus as defined in claim 8 wherein said elevation is formed by a O ring.

10. Apparatus as defined in claim 1 wherein said first pressure transmission element forms a lower area of said pressure sensor.

11. Apparatus as defined in claim 3, further comprising a pressure measuring chamber formed with two connectors for attachment of a tube for conducting the fluid, said second pressure transmission and said clamping fixture being arranged adjacent said pressure measuring chamber.

12. Apparatus as defined in claim 11 wherein said pressure measuring chamber is of cylindrical configuration.

13. Apparatus as defined in claim 12, further comprising a volume-reducing elevation in the area of said pressure measuring chamber in opposition to said second pressure transmission element.

14. Apparatus as defined in claim 13 wherein said volume-reducing elevation is of truncated cone shape.

15. Apparatus as defined in claim 1 wherein each of said first and second pressure transmission elements is provided in form of a membrane.

16. Apparatus as defined in claim 15 wherein said second pressure transmission element is a silicon membrane.

17. Use of an apparatus of claim 1 for non-invasive pressure measurement.

18. Use of an apparatus of claim 1 for non-invasive pressure measurement at a blood tube system.

19. Use of an apparatus of claim 1 for non-invasive pressure measurement at a blood tube system of a dialysis machine.

* * * * *